(12) United States Patent
Daisy et al.

(10) Patent No.: US 10,495,748 B2
(45) Date of Patent: *Dec. 3, 2019

(54) METHOD OF WALK-THROUGH SECURITY INSPECTION AND SYSTEM THEREOF

(71) Applicant: ROHDE & SCHWARZ GMBH & CO. KG, Munich (DE)

(72) Inventors: Ron Daisy, Raanana (IL); Amir Beeri, Zoran (IL)

(73) Assignee: ROHDE & SCHWARZ GMBH & CO. KG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/388,024

(22) Filed: Apr. 18, 2019

(65) Prior Publication Data

US 2019/0242990 A1 Aug. 8, 2019

Related U.S. Application Data

(63) Continuation of application No. 16/080,060, filed as application No. PCT/IL2017/051172 on Oct. 26, 2017, now Pat. No. 10,310,072.

(30) Foreign Application Priority Data

Oct. 30, 2016 (IL) .......................... 248615

(51) Int. Cl.
*G01S 13/88* (2006.01)
*G01N 23/046* (2018.01)
(Continued)

(52) U.S. Cl.
CPC .......... *G01S 13/887* (2013.01); *G01N 23/046* (2013.01); *G01S 13/0209* (2013.01);
(Continued)

(58) Field of Classification Search
CPC ...... G01S 13/887; G01S 13/90; G01N 23/046
(Continued)

(56) References Cited

U.S. PATENT DOCUMENTS 5,835,054 A * 11/1998 Warhus ................... G01S 7/292
342/22
7,430,257 B1 * 9/2008 Shattil ................... H04B 1/707
342/367
(Continued)

FOREIGN PATENT DOCUMENTS

CA      2895795 A1 * 12/2015 ............... G01V 3/12
CN    102914766         2/2013
(Continued)

*Primary Examiner* — Vladimir Magloire
*Assistant Examiner* — Nuzhat Pervin
(74) *Attorney, Agent, or Firm* — Browdy and Neimark, P.L.L.C.

(57) ABSTRACT

There are provided a security inspection system comprising ultra-wideband transmitters (104) and receivers (103) and a method of security inspection. The method comprises scanning a walk-through inspection space (200) along with an inspected person passing there through to yield collected data informative of scattered signals in association with respective channels, wherein the ultra-wideband transmitters and receivers are arranged at both sides of the inspection space. The method further comprises dividing the inspection space into a plurality of subspaces such that each voxel in the inspection space belongs to one and only one subspace, providing image reconstruction separately for each subspace of the plurality of the subspaces, wherein image reconstruction for voxels residing in a given subspace is provided using collected data corresponding to a set of channels selected for the given subspace in accordance with predefined rules; and using image reconstruction results to detect a concealed object.

20 Claims, 9 Drawing Sheets

(51) Int. Cl.
*G01V 3/12* (2006.01)
*G01S 13/02* (2006.01)
*G01S 13/90* (2006.01)
*G01S 13/89* (2006.01)

(52) U.S. Cl.
CPC ............ *G01S 13/90* (2013.01); *G01V 3/12* (2013.01); *G01S 13/89* (2013.01)

(58) Field of Classification Search
USPC .......................................................... 342/22
See application file for complete search history.

(56) References Cited

U.S. PATENT DOCUMENTS

| | | | | |
|---|---|---|---|---|
| 7,593,449 | B2* | 9/2009 | Shattil | H04B 1/707 375/130 |
| 7,965,761 | B2* | 6/2011 | Shattil | H04B 1/7174 375/147 |
| 8,050,740 | B2* | 11/2011 | Davis | A61B 5/05 324/637 |
| 8,861,588 | B2* | 10/2014 | Nguyen | G01S 13/90 341/155 |
| 9,363,024 | B2* | 6/2016 | Nguyen | H04B 15/00 |
| 9,405,990 | B2* | 8/2016 | Skatter | G06K 9/46 |
| 9,485,063 | B2* | 11/2016 | Shattil | H04B 7/026 |
| 2006/0058606 | A1* | 3/2006 | Davis | A61B 5/05 600/407 |
| 2007/0075889 | A1* | 4/2007 | Sheen | G01S 13/89 342/22 |
| 2007/0211786 | A1* | 9/2007 | Shattil | H04B 1/707 375/141 |
| 2007/0259632 | A1* | 11/2007 | Babakhani | H04B 1/04 455/129 |
| 2008/0284636 | A1* | 11/2008 | Hausner | G01V 3/12 342/22 |
| 2009/0110033 | A1* | 4/2009 | Shattil | H04B 1/7174 375/141 |
| 2009/0153392 | A1* | 6/2009 | Holbrook | G01N 22/00 342/22 |
| 2009/0238426 | A1* | 9/2009 | Fear | G06K 9/3216 382/128 |
| 2009/0294704 | A1* | 12/2009 | Zailer | H01Q 3/46 250/580 |
| 2009/0321638 | A1* | 12/2009 | Hu | G01N 1/02 250/336.1 |
| 2010/0072361 | A1* | 3/2010 | Liu | G01V 8/005 250/286 |
| 2010/0220001 | A1* | 9/2010 | Longstaff | G01S 7/414 342/22 |
| 2010/0295725 | A1* | 11/2010 | Krozer | G01S 13/003 342/25 A |
| 2012/0049863 | A1* | 3/2012 | Ostwald | G01S 7/411 324/642 |
| 2012/0127317 | A1* | 5/2012 | Yantek | G01V 8/14 348/156 |
| 2012/0250748 | A1* | 10/2012 | Nguyen | G01S 13/0209 375/224 |
| 2013/0082856 | A1* | 4/2013 | Paglieroni | G01S 13/90 342/22 |
| 2013/0236115 | A1* | 9/2013 | Nguyen | G01S 13/0209 382/260 |
| 2013/0244710 | A1* | 9/2013 | Nguyen | G01S 13/0209 455/501 |
| 2013/0335528 | A1* | 12/2013 | Vishwanath | G06T 17/00 348/46 |
| 2014/0055297 | A1* | 2/2014 | Beeri | G01S 13/89 342/21 |
| 2014/0341431 | A1* | 11/2014 | Chen | G01V 8/005 382/103 |
| 2014/0347213 | A1* | 11/2014 | Nguyen | H04B 15/00 342/25 F |
| 2015/0244430 | A1* | 8/2015 | Shattil | H04B 1/0003 370/254 |
| 2015/0253422 | A1* | 9/2015 | Morton | G01S 13/887 324/642 |
| 2015/0379356 | A1* | 12/2015 | Nikolova | G01V 3/12 342/90 |
| 2019/0004170 | A1* | 1/2019 | Morton | G01S 13/887 |

FOREIGN PATENT DOCUMENTS

| | | | |
|---|---|---|---|
| WO | 2011/128418 A1 | 10/2011 | |
| WO | WO-2013173465 A1 * | 11/2013 | ............ G06T 17/00 |
| WO | 2015/086524 A1 | 6/2015 | |
| WO | WO-2015110564 A1 * | 7/2015 | ............ G01V 8/005 |
| WO | 2016161362 A1 | 10/2016 | |
| WO | WO-2016161362 A1 * | 10/2016 | ............ G01V 8/005 |

* cited by examiner

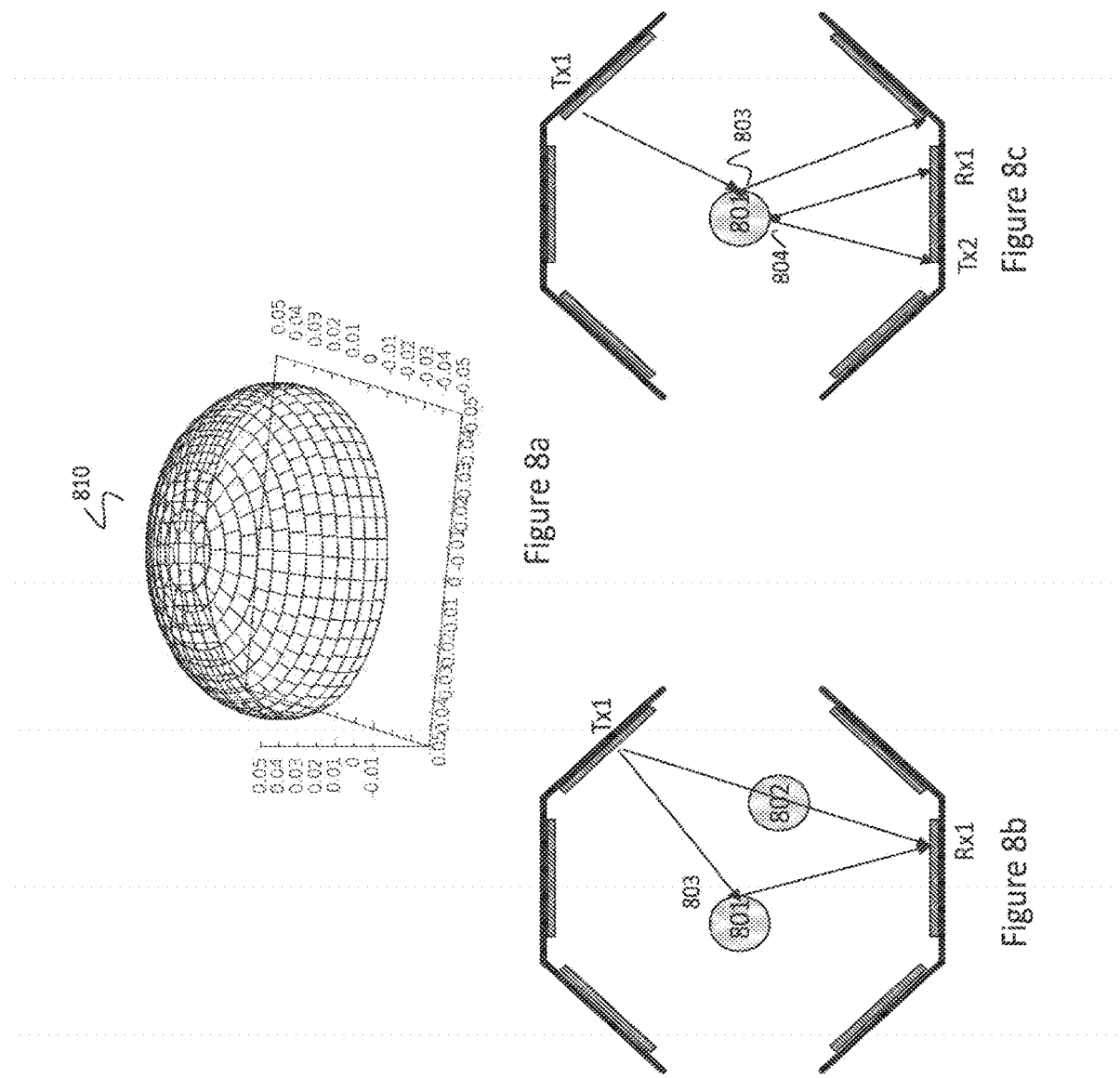

METHOD OF WALK-THROUGH SECURITY INSPECTION AND SYSTEM THEREOF

TECHNICAL FIELD

The presently disclosed subject matter relates to security inspection and, more particularly, a system and methods of a walk-through security inspection of persons.

BACKGROUND

Security inspection technology and apparatuses are extensively applied in airports, railway stations, seaports and other important sites needing to carry out security inspection of persons' bodies. Known security inspection systems include a variety of concealed weapon detection (CWD) systems exploiting different physical principles to discover undesirable objects hidden under persons' clothing. Conventional security inspection systems currently in place at security checkpoints include metal detectors, X-ray systems and millimeter wave systems. However, metal detectors are prone to false alarms, and are not capable of detecting non-metallic objects. X-rays-based systems have deployment problems in view of their inherent radiation hazard and, also, are not able to detect certain materials/geometries (e.g. ceramic knives). As an alternative to existing systems, there have been proposed various microwave imaging systems having the ability to penetrate clothing to image concealed items.

Problems of microwave-based security inspection have been recognized in the conventional art and various techniques have been developed to provide solutions, for example:

US Patent Application No. US2008/0284636 discloses a method and apparatus for detecting objects when a person entering a secured zone is illuminated with low-power polarized radio waves. Differently polarized waves which are reflected back from the person are collected. Concealed weapons are detected by measuring various parameters of the reflected signals and then calculating various selected differences between them. These differences create patterns when plotted as a function of time. Preferably a trained neural network pattern recognition program is then used to evaluate these patterns without creating an image of the object and autonomously render a decision on the presence of a weapon or other object. An interrupted continuous wave system may be employed. Multiple units may be used to detect various azimuthal angles and to improve accuracy. The units may be used in a bi-static configuration which enables comparison of off-axis signals.

US Patent Application No. US2010/0220001 discloses a radar imaging system for capturing an image of an object within an area of interest through at least one visual impairment. The radar imaging system comprises at least one radar array. The radar array includes a plurality of transmitter elements and a plurality of receiver elements for receiving a plurality of coded return signals from an object through the at least one visual impairment. The system further comprises at least one processor coupled to the transmitter and receiver elements, which is adapted to transmit a plurality of differently coded signals toward the object and the at least one visual impairment; decode the plurality of coded return signals received by each of the receiver elements; extract from the decoded return signals a multiplicity of captured signals for each transmitter to receiver path; focus the multiplicity of signals on all points of interest within the area of interest by aligning the multiplicity of captured signals to be co-incident from a particular point within the area of interest; and sum the aligned signals to produce an image of the object.

US Patent Application No. US2012/0049863 discloses a method for detecting a covered dielectric object, where a microwave signal that can be modified in frequency is generated at a particular bandwidth and transmitted in the direction of the covered dielectric object. The microwave signal reflected by the object is then obtained from the three-dimensional measurement result in a lateral, two-dimensional pattern, a highest signal amplitude and a second-highest signal amplitude within a particular time period before or after the received microwave signal is identified in a plurality of pattern points of the pattern. The object is detected if an accumulation of pattern points of the pattern is present, in which the difference in each case between the highest and the second highest signal amplitude of the received microwave signal is less than a defined threshold value.

US Patent Application No. US2013/0082856 discloses a method and system for detecting the presence of subsurface objects within a medium. The imaging and detection system can operate in a multi-static mode to collect radar return signals generated by an array of transceiver antenna pairs that is positioned across the surface and that travels down the surface. The imaging and detection system pre-processes the return signal to suppress certain undesirable effects. The imaging and detection system then generates synthetic aperture radar images from real aperture radar images generated from the pre-processed return signal. The imaging and detection system then post-processes the synthetic aperture radar images to improve detection of subsurface objects. The imaging and detection system identifies peaks in the energy levels of the post-processed image frame, which indicates the presence of a subsurface object.

US Patent Application No. US2014/0341431 discloses a through-type of millimeter wave person body security inspection system, wherein a person to be inspected passes through an inspect passage therein for performing a security inspection. The disclosed security inspection system can make a total body dynamic scanning to the person to be inspected, and obtain millimeter wave images and optical images with respect to the person body, thereby achieving the inspection of prohibited articles hidden within clothing of the person body and an automatic alarm thereof.

US Patent Application No. US2015/0379356 discloses a system and method for detecting concealed weapons. A radiofrequency transmitter transmits an RF signal stream into a region of interest. An RF receiver receives a scattered signal stream from the region of interest. The scattered signal stream is generated in the region of interest from the radiofrequency signal stream when a target is at least partially within the region of interest. A plurality of resonant signal components are identified from the scattered signal stream. Preprocessed resonant signal components are generated by removing environmental signal components. A target assessment is determined from the preprocessed resonant signal components using a trained statistical model. A target response is triggered if the target assessment indicates that a weapon is detected on the target.

International Patent Application No. WO15/086524 discloses a method for capturing a 360-degree 3D view of the surface of a moving human or animal's body. The method comprises the steps of: (A) determining a speed of motion of at least one area of the body surface; and B) capturing at least said area of the body surface at a point in time when the value of the speed of motion of the area is lower than a defined threshold value.

The references cited above teach background information that may be applicable to the presently disclosed subject matter. Therefore the full contents of these publications are incorporated by reference herein where appropriate for appropriate teachings of additional or alternative details, features and/or technical background.

GENERAL DESCRIPTION

In accordance with certain aspects of the presently disclosed subject matter, there is provided a method of security inspection by a security inspection system comprising ultra-wideband transmitters and receivers, the method comprising: scanning a walk-through inspection space along with an inspected person passing there through to yield collected data informative of scattered signals in association with respective transmit/receive channels, wherein the ultra-wideband transmitters and receivers are arranged at both sides of the inspection space; upon dividing the inspection space into a plurality of subspaces such that each voxel in the inspection space belongs to one and only one subspace, providing image reconstruction separately for each subspace of the plurality of the subspaces, wherein image reconstruction for voxels residing in a given subspace is provided using collected data corresponding to a set of channels selected for the given subspace in accordance with predefined rules; and using image reconstruction results to detect a concealed object.

The method can further comprise, for each given subspace: calculating one or more parameters of specular points of channels reflected by a virtual equi-area tessellated sphere co-centric with a given subspace; identifying channels with the calculated one or more parameters matching channel-dropping criteria defined to the given subspace thereby giving rise to omitted channels; and generating a set of channels selected for the given subspace, the set generation comprises excluding the omitted channels from further processing for image reconstruction.

In accordance with other aspects of the presently disclosed subject matter, there is provided a security inspection system comprising a signal acquisition unit operatively connected to data processing unit. The signal acquisition unit comprises a plurality of ultra-wideband transmitters and receivers arranged at both sides of a walk-through inspection space and configured to scan the inspection space along with an inspected person passing there through, to yield collected data informative of scattered signals in association with respective channels. The data processing unit is configured: upon dividing the inspection space into a plurality of subspaces such that each voxel in the inspection space belongs to one and only one subspace, to provide image reconstruction separately for each subspace of the plurality off the subspaces, wherein image reconstruction for voxels residing in a given subspace is to be provided using collected data corresponding to a set of channels selected for the given subspace in accordance with predefined rules; and to use image reconstruction results for detecting a concealed object.

The data processing unit can be further configured, for each given subspace: to calculate one or more parameters of specular points of channels reflected by a virtual equi-area tessellated sphere co-centric with a given subspace; to identify channels with the calculated one or more parameters matching channel-dropping criteria defined to the given subspace thereby giving rise to omitted channels; and to generate a set of channels selected for the given subspace, the set generation comprises excluding the omitted channels from further processing for image reconstruction.

In accordance with further aspects and, optionally, in combination with other aspects of the presently disclosed subject matter, generating a set of channels selected for a given subspace can further comprise matching the amount of channels remaining after excluding the omitted channels to a predefined for the given subspace number $N_{ch}$ of selected channels. When the amount of remaining channels is less than $N_{ch}$, the set generation can comprise adding dummy channels. When the amount of remaining channels is more than $N_{ch}$, the set generation can further comprise excluding a part of remaining channel from further processing for image reconstruction, wherein the part of remaining channel is excluded so as to maximize uniformity of coverage of a predefined part of the virtual sphere by specular points of non-excluded channels.

In accordance with further aspects and, optionally, in combination with other aspects of the presently disclosed subject matter, the channel-dropping criteria can comprise one or more criteria selected from a group consisting of: absence of a specular point on a respective sphere, reflection angle more than a predefined maximal reflection angle, and max bore-sight angle for a receiver and/or for a transmitter more than a predefined maximal bore-sight angle.

Alternatively or additionally, the channel-dropping criteria can comprise one or more criteria related to location of respective specular points on the sphere.

In accordance with further aspects and, optionally, in combination with other aspects of the presently disclosed subject matter, inspection subspaces can be combined in two or more groups corresponding to location in the inspection space, and channel-dropping criteria defined to subspaces in a given group can comprise at least one criteria with values being common for all subspaces in the given group and being different for subspaces in another group.

Among advantages of certain embodiments described above is capability of selecting channels that are mostly appropriate for achieving optimal 3D image reconstruction performance matching real time requirements, signal/noise requirements, compute constrains, and/or other performance-related requirements.

BRIEF DESCRIPTION OF THE DRAWINGS

In order to understand the invention and to see how it can be carried out in practice, embodiments will be described, by way of non-limiting examples, with reference to the accompanying drawings, in which:

FIG. 8a schematically illustrates an example of an equi-area tessellated sphere usable in certain embodiments of the presently disclosed subject matter; and FIGS. 8b and 8c schematically illustrate exemplified specular points.

DETAILED DESCRIPTION

In the following detailed description, numerous specific details are set forth in order to provide a thorough understanding of the invention. However, it will be understood by those skilled in the art that the presently disclosed subject matter may be practiced without these specific details. In other instances, well-known methods, procedures, components and circuits have not been described in detail so as not to obscure the presently disclosed subject matter.

Unless specifically stated otherwise, as apparent from the following discussions, it is appreciated that throughout the specification discussions utilizing terms such as "scanning", "calculating", "comparing", "generating", "matching", "dividing" or the like, refer to the action(s) and/or process(es) of a computer that manipulate and/or transform data into other data, said data represented as physical, such as electronic, quantities and/or said data representing the physical objects. The term "computer" should be expansively construed to cover any kind of hardware-based electronic device with data processing capabilities including, by way of non-limiting example, respective parts of security inspection system disclosed in the present application.

The terms "non-transitory memory" and "non-transitory storage medium" used herein should be expansively construed to cover any volatile or non-volatile computer memory suitable to the presently disclosed subject matter.

The operations in accordance with the teachings herein may be performed by a computer specially constructed for the desired purposes or by a general-purpose computer specially configured for the desired purpose by a computer program stored in a non-transitory computer-readable storage medium.

Embodiments of the presently disclosed subject matter are not described with reference to any particular programming language. It will be appreciated that a variety of programming languages may be used to implement the teachings of the presently disclosed subject matter as described herein.

Figure 1:
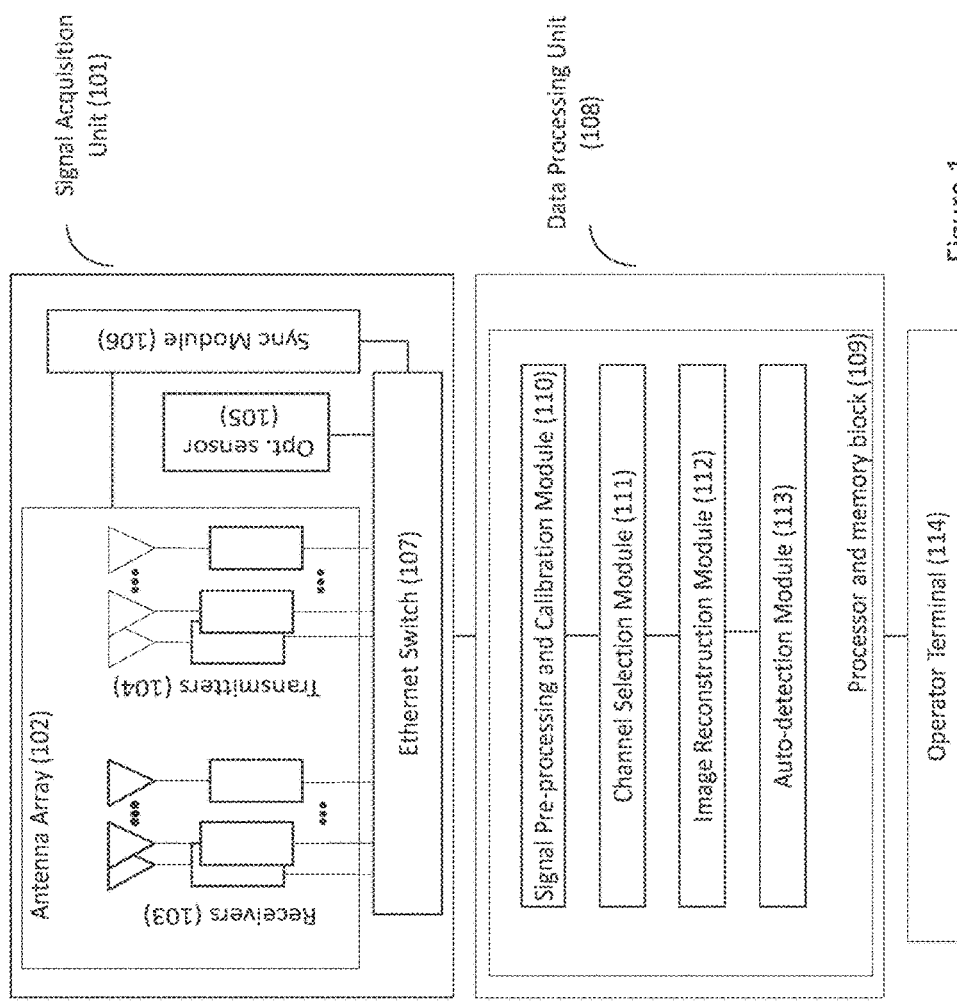
FIG. 1 illustrates a functional block diagram of a security inspection system (SIS) in accordance with certain embodiments of the presently disclosed subject matter.

Bearing this in mind, attention is drawn to FIG. 1 illustrating a functional block diagram of a security inspection system (SIS) in accordance with certain embodiments of the presently disclosed subject matter. SIS comprises signal acquisition unit 101 operatively connected to data processing unit 108 which is further operatively connected to operator terminal 113. By way of non-limiting example, SIS structural elements implementing the above functional units can be connected via an Ethernet network thereby enabling wide band communication channel between the different SIS parts.

For purpose of illustration only, the following description is provided for time-domain image reconstruction based on ultra-wide band pulses at the transmitter output. Those versed in the art will readily appreciate that the teachings of the presently disclosed subject matter are, likewise, applicable to other transmit/receive techniques such as, for example, FMCW (frequency-domain imaging).

Signal acquisition unit 101 can be arranged as a gate providing a two-sided passageway with inspection space which is at least partly isolated from an ambient environment. By way of non-limiting example, the inspection space can be constituted by a passageway between two groups of panels located at two sides of the passageway and bearing transmitters and receivers distributed thereover. An inspected person is scanned by means of microwave radiation white walking through the gate in an undisturbed movement flow.

The signal acquisition unit is configured to transmit, from different directions, ultra-wide band (UWB) pulse signals to the inspection space, and to sample the received scattered signals, thereby enabling two-sided scanning of a person to be inspected during his/her walking through the passageway. Signal acquisition unit 101 comprises sensor array 102 operatively connected to Ethernet switch 107 and to synchronization module 106 which is also operatively connected to Ethernet switch 107. Signal acquisition unit can further comprise an optical sensor (e.g. video camera) 105 and, optionally, environment sensors (not shown) operatively connected to the synchronization module 106.

Sensor array 102 comprises a plurality of spatially separated transmitters 104 and a plurality of spatially separated receivers 103 arranged in one or more antenna arrays operating in mono-static or multi-static modes, wherein each transmitter and each receiver can have horizontal or vertical polarization. Each pair of transmitter and receiver forms a spatially distinct channel characterized by the respective transmitter and receiver and their polarization states.

Figure 2A:
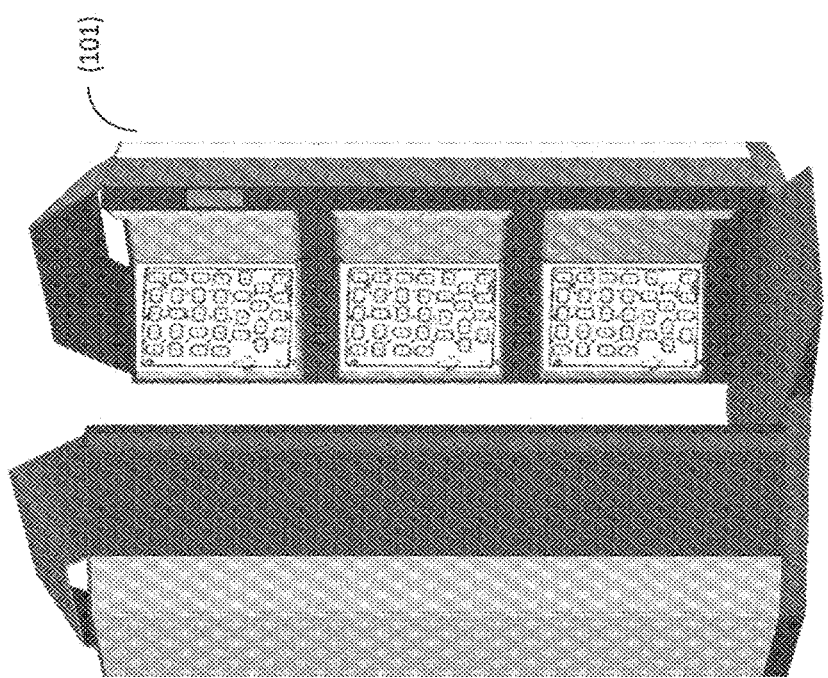
FIG. 2a illustrates a generalized side view of an exemplified signal acquisition unit in accordance with certain embodiments of the currently presented subject matter.
Figure 2B:
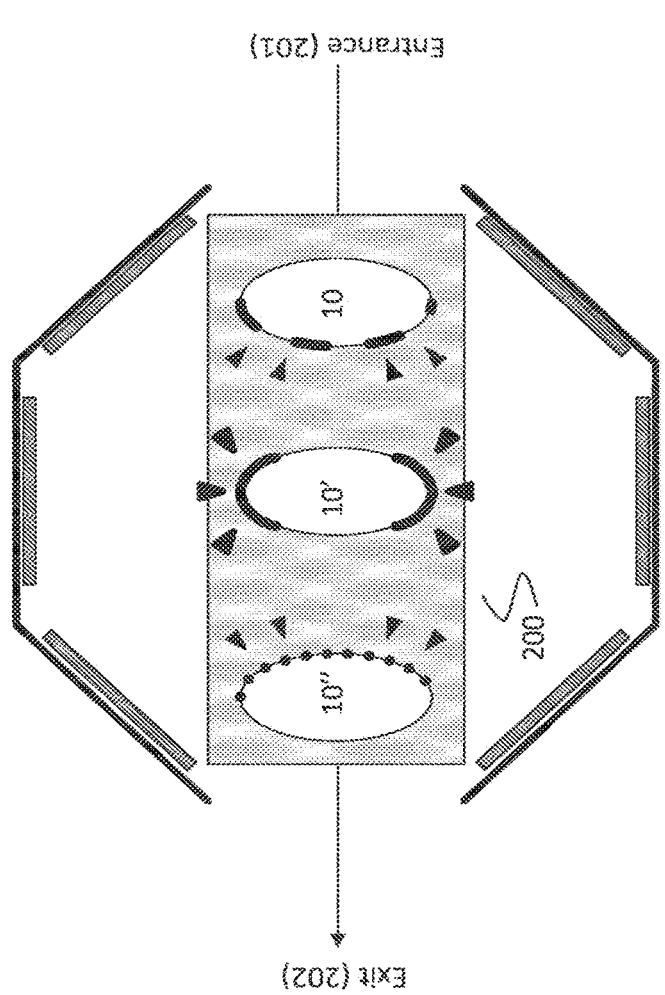
FIG. 2b illustrates a generalized top view of the exemplified signal acquisition unit in accordance with certain embodiments of the currently presented subject matter.

A generalized view of an exemplified signal acquisition unit is illustrated in FIG. 2a (side view) and FIG. 2b (top view). The illustrated exemplified signal acquisition unit 101 is arranged as an octagonal gate in which two opposing faces (entrance and exit) are removed to allow subjects to be inspected to pass through for inspection. Transmitters/receivers of the sensor array are distributed over the panels so to enable two-sided imaging of, substantially, the entire inspection space. For simplicity of illustration, only one of the panels (nominated as 101-a) is illustrated with transmitters/receivers therein. Depending on certain embodiments, the inspection space can be configured as the entire space between the panels, as a rectangular 200 between predefined entrance plane 201 and exit plane 202 or otherwise.

It is noted that the teachings of the currently disclosed subject matter are not bound by the form of the two-sided gate and/or parts thereof. By way of non-limiting example, the gate can have a cylindrical or 3D-polyhedron (with at least three facets at each side) form with openings for entrance and exit. Optionally, the two-sided gate can further comprise a top covering and/or floor of the passageway also bearing the receivers/transmitters involved in the signal acquisition. Optionally, a form of one side of the gate can differ from the form of another side of the gate.

As illustrated by way of non-limiting example in FIG. 2a, UWB transmitters and receivers can be arranged in a plurality of transmit/receive boards (illustrated for panel 101-a as 102-1, 102-2 and 102-3), each comprising a plurality of transmitters and a plurality of receivers. Each transmit/receive board further comprises a digital controller (not shown) with an Ethernet interface configured to enable connection of the board to Ethernet switch 107 (not shown in FIG. 2a). Synchronization module 106 (not shown in FIG.

2a) is configured to enable synchronizing the operation of the transmit/receive boards and transmitters/receivers therein. By way of non-limiting example, sensor array 102 can have eighteen boards (3 boards/panel), a given board can comprise sixteen transmitters and sixteen receivers operating in 3-12 GHz frequency band, connected to horizontal or vertical polarization oriented non-dispersive antenna supporting the same frequency band. Each pair of transmitter and receiver forms a spatially distinct channel characterized by the respective transmitter and receiver and polarization states thereof. The exemplified sensor array has 82944 channels which can be divided into three groups according to their polarization states.

Referring back to FIG. 1, signal acquisition unit 101 is configured to transfer the digitized acquired samples of scattered signals to data processing unit 108, each sample being transferred in association with its respective channel. Depending on certain embodiments, the acquired samples can be transferred as a continuous stream or can be buffered, before transferring, per frame, per group of frames and/or otherwise.

Data processing unit 108 is configured to receive the digitized channel-associated samples from signal acquisition unit 101 and provide further processing thereof. Data processing unit 108 comprises processor and memory block 109 and can be implemented on one or more computers operatively connected to the inspection gate (e.g. via Ethernet network). Processor(s) of the processor and memory block (PMB) 109 can be configured to execute several functional modules in accordance with computer-readable instructions implemented on a non-transitory computer-readable storage medium of block 109. Such functional modules are referred to hereinafter as comprised in the processor and memory block 109.

The processor and memory block 109 comprises operatively connected signal pre-processing and calibration module 110, channel selection module 111, image reconstruction module 112 and auto-detection module 113. Signal pre-processing and calibration module 119 is configured to provide calibration to compensate transmit/receive timing drifts and/or deformations of mechanical structures as well as necessary filtering, shaping, etc. thereby giving rise to collected data usable for further processing (referred to hereinafter as collected data). Channel selection module 111 is configured to select, in accordance with predefined rules, channels to be used for image reconstruction. Image reconstruction module 112 is configured to use part of collected data associated with the selected channels to generate a set of voxels corresponding to 3D image of the inspected person. Auto-detection module 113 is configured to analyze the generated set(s) of voxels to automatically detect the existence and location of concealed objects on the scanned body. Optionally, the PMB 109 cart further comprise volume rendering block (not shown) configured to use the generated set of voxels to generate one or more projected 2D images of the body (including the detected objects, if any). Rendering can be provided from different projection viewpoints. Operation of PMB 109 and the functional blocks therein will be further detailed with reference to FIGS. 4-8.

In accordance with certain embodiments of the presently disclosed subject matter, SIS can be configured to dominantly collect data from different regions of a body in a predefined dependency on the person's location within the passageway. For example, when the person is located at the entrance (position 10 in FIG. 2*b*), SIS is configured to dominantly collect data from the front side of the body (illustrated by dashed lines in FIG. 2*b*); when the person is located at the center (position 10' in FIG. 2*b*), SIS is configured to dominantly collect data from the sides of the body (illustrated by bold lines in FIG. 2*b*); and when the person is located at the gate exit (position 10" in FIG. 2*b*), SIS is configured to dominantly collect data from its rear (illustrated by dotted lines in FIG. 2*b*). As will be further detailed with reference to FIGS. 5-8, final all-round image reconstruction can be provided using sets of voxels, each set generated using data collected from a respective image-capture region when the person walks through the gate.

Figure 3:
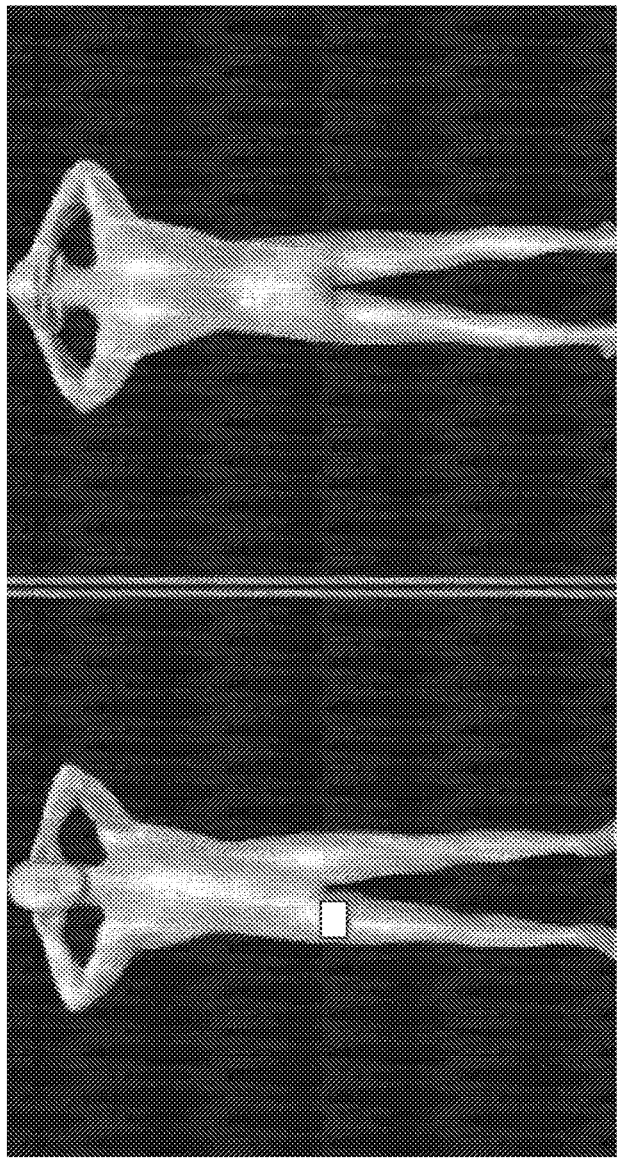
FIG. 3 illustrates an exemplified image generated by the SIS and rendered at an operator terminal.

Data processing unit 108 is further configured to transfer voxels' processing results for displaying at computer-based operator terminal 113. Operator terminal 113 can be also configured to operate as a user interface enabling an operator to have control over the SIS operation (ON/OFF, modes, etc.). As illustrated by way of non-limiting example in FIG. 3, the results of voxel processing can be displayed in different modes: for example, in auto-detection mode in which a detected concealed object is displayed on an avatar (FIG. 3) or/and as 2D body images (with detected, if any, non-body objects on the body surface) rendered from front-back, left, and right viewpoints. It is noted that the processing necessary for overlaying the detected concealed object on the avatar can be provided at data processing unit 108 and/or operator terminal 113.

It is noted that the teachings of the presently disclosed subject matter are not bound by the SIS system described with reference to FIG. 1. Equivalent and/or modified functionality can be consolidated or divided in another manner and can be implemented in any appropriate combination of software with firmware and/or hardware and executed on suitable devices. The units of SIS system can be standalone entities, or can be integrated, fully or partially, with other entities.

Figure 4:
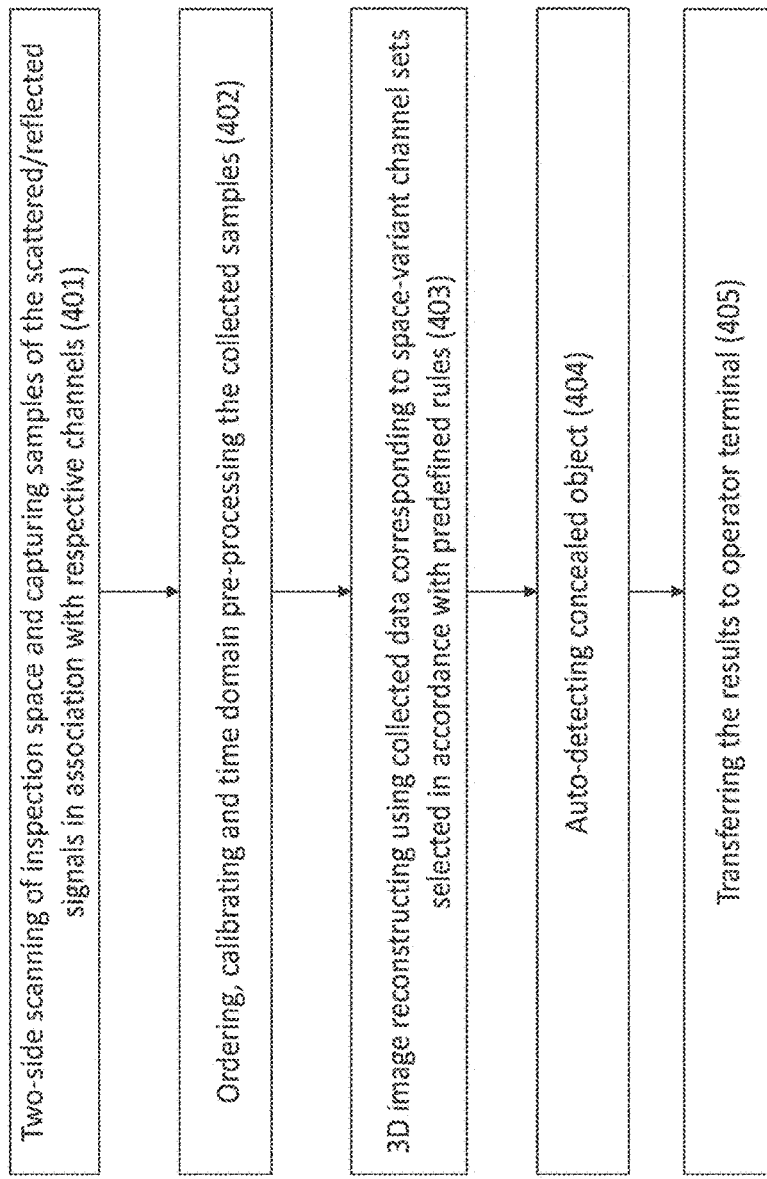
FIG. 4 illustrates a generalized flow-chart of operating the SIS in accordance with certain embodiments of the presently disclosed subject matter.

Referring to FIG. 4, there is illustrated a generalized flow chart of operating the security inspection system (SIS) in accordance with certain embodiments of the presently disclosed subject matter.

Sensor array is configured to define a sequence of operations of the transmitters such that each transmitter of the plurality of M transmitters is provided with a predefined transmission time slot within a transmission frame. Upon initiating the signal acquisition process, each transmitter transmits, during respectively assigned time slots, UWB pulses at a constant repetition rate, one transmitter at a time. Each receiver of the plurality of N receivers samples the scattered signals, producing L time domain samples. Thereby, for each time slot (i.e. for each transmitter), signal acquisition unit produces N*L time domain samples, and produces M*N*L time domain samples per frame. Each acquired sample is associated with a channel characterized by respective transmitter, receiver and polarization thereof.

By way of non-limiting example, the signal acquisition process can be initiated and terminated manually by an operator and/or be automatically responsive to data indicative of respective location (e.g. gate entrance 201 and gate exit 202) of the inspected person. By way of non-limiting example, such data can be received from one or more optical sensors 105, weight sensors or any other sensors capable to provide information that the inspected person is at the respective locations predefined as start/end for the signal acquisition process. Alternatively, SIS can be configured to provide the signal acquisition process continuously, frame after frame, regardless of the person's location in the passageway.

Thus, the signal acquisition unit scans (401) the inspection space along with the inspected person walking through such space, and captures samples of the scattered signals, each sample associated with a respective channel.

The digitized captured samples are transferred to data processing unit 108 for further processing. The samples can be transferred and/or processed as a continuous stream, per frame or per group of sequential frames, etc.

Upon ordering the received time domain samples, data processing unit 108 provides (402) calibration and time domain pre-processing of the calibrated signals. Time domain pre-processing can include equalization, background removal, delay compensation, etc. Data processing unit 108 further provides (403) 3D image reconstruction using data corresponding to space-variant channel sets selected in accordance with predefined rules.

By way of non-limiting example, a 3D image can be reconstructed with the help of a back projection technique. The back projection technique includes calculating the contribution of each respective channel into each given voxel, and calculating the overall value of a given voxel as the sum of all time-domain values associated with each one of the respective channels. Going over all respective channels yields a voxel value and going over all voxels yields a 3D image. As will be further detailed with reference to FIGS. 5-8, the channels' selection for calculating voxel's value is space-variant and can vary depending on location of the respectively reconstructing sub-space in the inspection space and/or location of the inspected person in the inspection space.

The efficiency of 3D image reconstruction can be further improved by applying a multi-grid approach.

It is noted that image reconstruction is not bound by back projection technique and the selected channel-associated data can be processed using other image reconstruction techniques (e.g. algebraic reconstruction, etc.) providing a set of voxels.

Referring back to FIG. 4, data processing unit 108 further processes the generated set of voxels to detect (404) cone object(s), if any; provides necessary rendering and transfers (405) the results to an operator terminal. By way of non-limiting example, detecting of concealed objects can be provided by analyzing surface features of the reconstructed image of the inspected body.

In certain embodiments, operations 401-406 are provided in a per-frame computational pipe. Optionally, the computation pipe can operate per a group of a predefined number N>1 of sequential frames; in such a case the collected data are further associated with a time stamp indicative of a respective acquisition frame.

Figure 5:
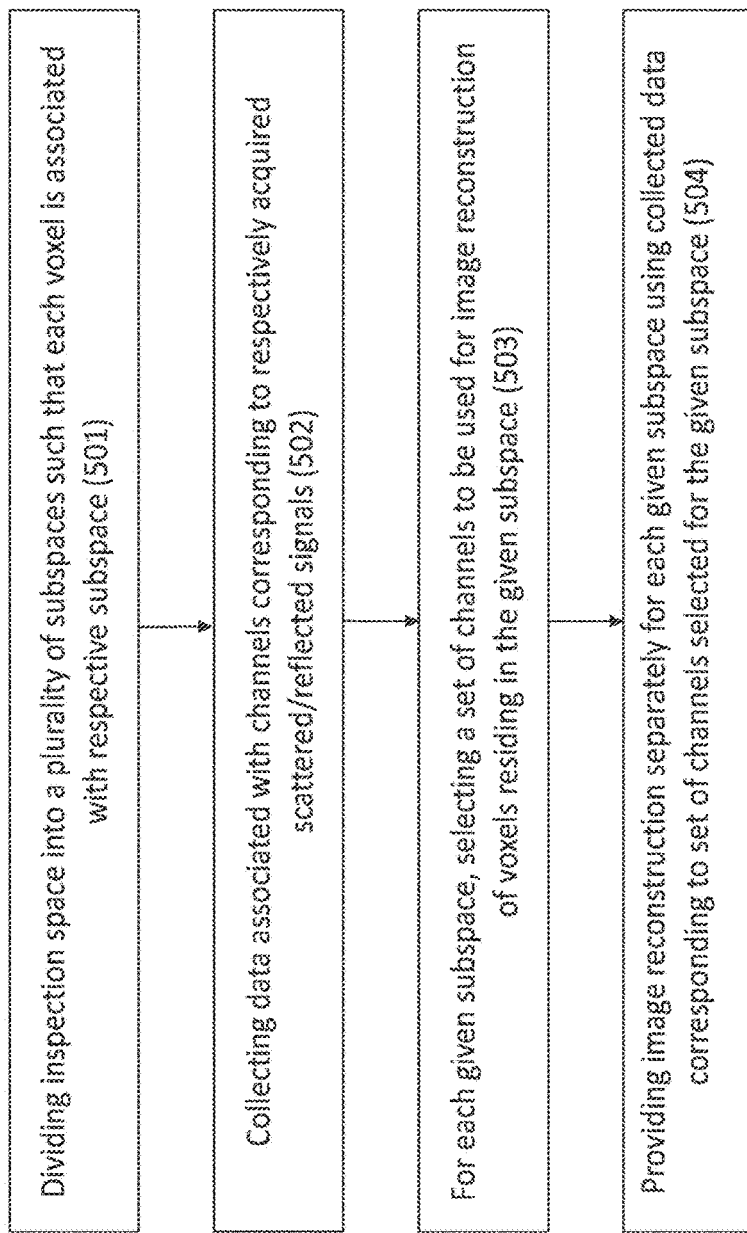
FIG. 5 illustrates a generalized flow chart of image reconstruction based on space-variant channel selection in accordance with certain embodiments of the presently disclosed subject matter.
Figure 7B:
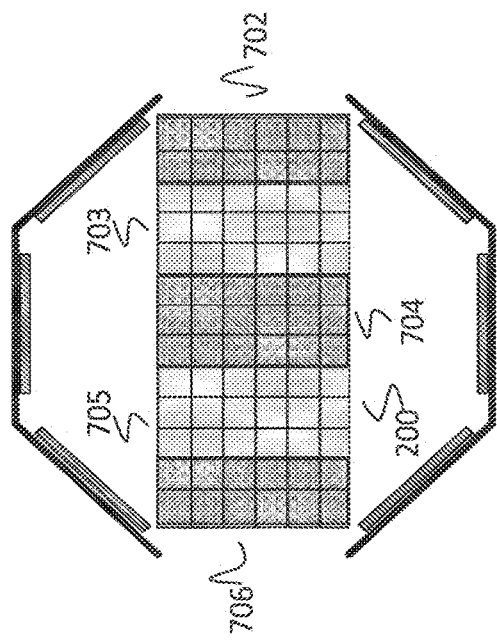
FIGS. 7a and 7b illustrate non-limiting examples of a plurality of inspection subspaces.
Figure 7A:
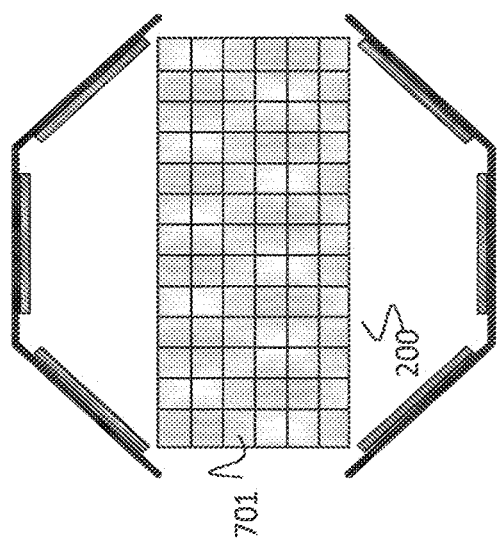

Referring to FIG. 5, there is illustrated a generalized flow chart of image reconstruction based on space-variant channel selection. In accordance with certain embodiments of the presently disclosed subject matter, the inspection space is divided (501) into a plurality of inspection subspaces such that each voxel in the inspection space belongs to one, and only one, subspace. Coordinates of subspaces (and/or rules of defining thereof) can be stored in the PMB 109. FIG. 7a illustrates a non-limiting example of a grid of inspection subspaces provided by dividing the inspection space 200 into equal subspaces (denoted as 701) with a predefined size (e.g. 5*5*5 cm).

Upon collecting (502) data associated with respective channels, PMB 109 further selects (503), for each given inspection subspace, a set of channels to be used for image reconstruction for voxels residing in the given inspection subspace. Optionally, prior to selecting the channels, PMB 109 can define contributing channels for each inspection subspace (i.e. channel contributing non-zero time domain value into the voxels of subspace), and select channels to be used for image reconstruction among the respective contributing channels. The selected sets of channels are space-variant, and can be selected in accordance with predefined rules, as will be further detailed with reference to FIGS. 6-8. For each subspace, PMB 109 further uses collected data corresponding to the set of channels selected to a given subspace, to provide (504) image reconstruction for the given subspace.

Figure 6:
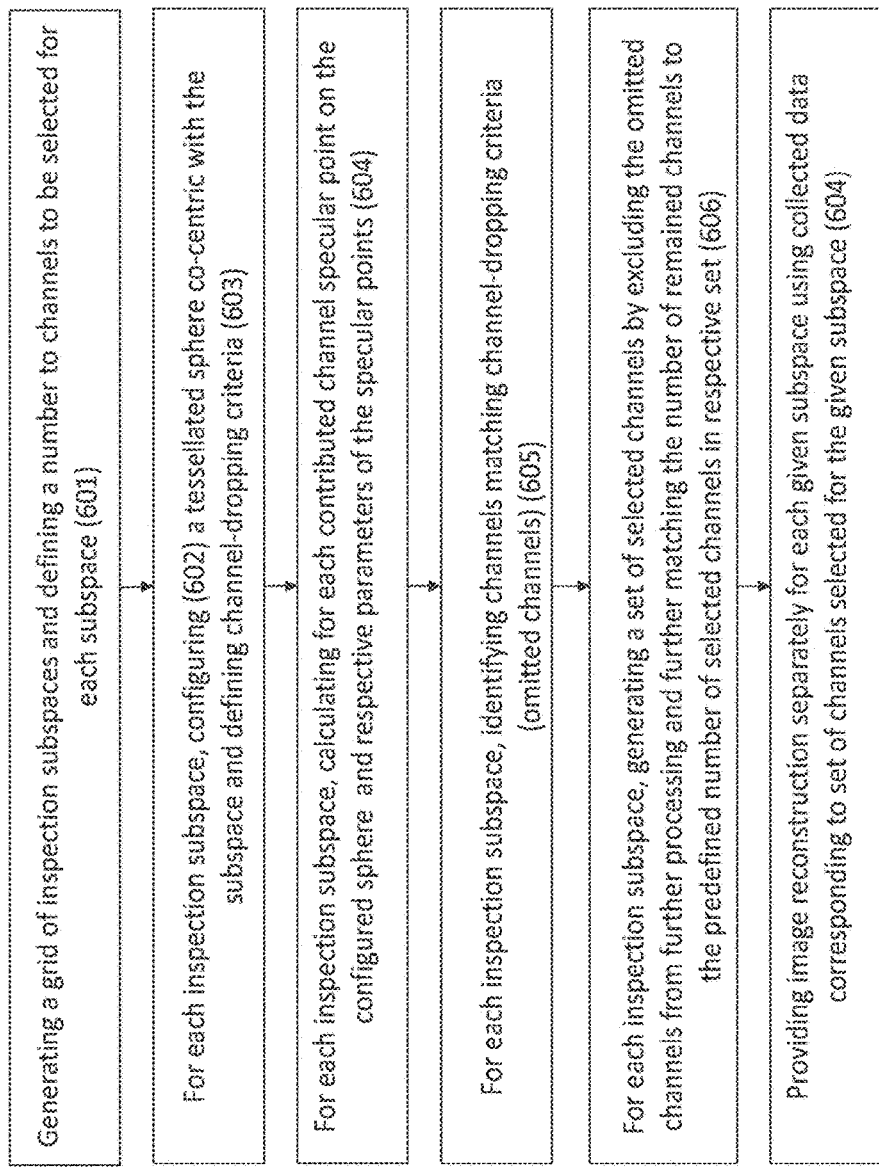
FIG. 6 illustrates a generalized flow chart of space-variant channel selection in accordance with certain embodiments of the presently disclosed subject matter.

Referring to FIG. 6, there is illustrated a generalized flow chart of space-variant channel selection in accordance with certain embodiments of the presently disclosed subject matter. PMB 109 is configured to logically divide the inspection space into a plurality (e.g. a grid) of inspection subspaces as detailed above, and to store a predefined number of channels $N_{ch}$ to be selected for each subspace. Optionally, although not necessary so, the number $N_{ch}$ can be defined equal to all subspaces. It is noted that, optionally, the number $N_{ch}$ can be predefined as "any available" or "any not less than a predefined minimal number" or "any not more than a predefined maximal number".

In accordance with certain embodiments of the presently disclosed subject matter, channel selection can be provided by analyzing specular points (i.e. points corresponding to equal incident and reflection angles) of channels reflected by a sphere. By way of non-limiting example, the entire sphere can be divided into patches all with the equal area as schematically illustrated in FIG. 8a, such sphere is referred to hereinafter as an equi-area tessellated sphere 810. PMB 109 configures (602), for each inspected subspace, a virtual equi-area tessellated sphere co-centric with the subspace; such sphere usable for calculating specular points for channels contributing to respective subspace. The size of the configured virtual sphere can be equal to the size respective subspace or constitute a substantial part thereof (e.g. size of the sphere can be 0.7-0.9 of the size of the subspace).

PMB 109 further stores a configuration defining, for each subspace, channel-dropping criteria (603). The term "channel-dropping criteria" used in this patent specification should be expansively construed to include any compound criterion, including, for example, several criteria and/or their logical combinations. In certain embodiments, channel-dropping criteria are matched when a match to at least one of criteria comprised therein, exists. In other embodiments, channel dropping criteria is matched when exists a match to predefined logical combination of at least part of criteria comprised therein.

Channel-dropping criteria can be related to parameters of specular points calculated with regard to respective spheres. For a given channel, such parameters can include: existence or absence of a specular point on a respective sphere (a specular point is considered as absent on a given sphere if a line connecting transmitter and receiver of the given channel intersects the given sphere); reflection angle for specular point (the angle between the incident ray and the sphere normal); bore-sight angles (the angle $\alpha_{TX}$ between the incident ray and the Tx bore-sight direction and the angle $\alpha_{RX}$ between the reflected ray and the RX bore-sight direction), etc.

For a given transmitter/receiver pair, parameters of a specular point depend on respective subspace, i.e. on location of respective sphere in the inspection space. For example, as illustrated in FIG. 8b, a channel between transmitter Tx1 and receiver Rx1 has a specular point 803 on sphere 801 and has no specular point on sphere 802 corresponding to another subspace.

Thus, channel-dropping criteria can comprise one or more criteria selected from group consisting of: absence of a specular point on a respective sphere, reflection angle more than a predefined maximal reflection angle $\max(\alpha_{TX}, \alpha_{RX})$ more than a predefined maximal bore-sight angle, etc. Optionally, but not necessary so, channel-dropping criteria can be configured as the same for each subspace. Alternatively, at least some of the criteria comprised in the channel-dropping criteria (and/or logical combination thereof) can be configured differently for different subspaces and/or groups thereof.

It is noted that the channel-dropping criteria for each subspace, can be preconfigured and/or can be configurable during SIS operation by an operator and/or automatically based on a feedback from image reconstruction results.

Alternatively or additionally, parameters of specular points can be indicative of location of a specular point on the respective sphere, and channel-dropping criteria can comprise criteria related to such a location. By way of non-limiting example, channel-dropping criteria can specify that all channels with specular points on one or more patches with predefined location shall be dropped.

Inspection subspaces can be combined in several groups corresponding to location in the passageway, and channel dropping criteria for all subspaces in the group can compose common location-related criteria. As illustrated in FIG. 7b, group 702 of subspaces corresponds to position 10 in FIG. 2b, group 704 of subspaces corresponds to position 10' in FIG. 2b, group 796 of subspaces corresponds to position 10" in FIG. 2b, and groups 703 and 705 correspond to intermediate positions. Accordingly, for subspaces in group 702 location-related criteria in the channel-dropping criteria can specify that channels (if any) with specular points on the right half of respected spheres shall be dropped; for subspaces in group 704 location-related criteria in the channel-dropping criteria can specify that channels with specular points on more than a predefined distance from top and/or bottom of respective spheres shall be dropped; for subspaces in group 706 location-related criteria in channel-dropping criteria for can be defined as location of specular points (if any) on the left half of respected spheres, etc.

Additionally or alternatively to the criteria above, the channel-dropping criterion can comprise the following criteria: for a subspace in a middle part of the inspection space (e.g. subspaces in group 704) drop any channel with specular point which does not correspond to transmitter/receiver pairs located on the same side of inspection space with regard to the path direction. This criteria is illustrated in FIG. 8c: for the same sphere 801 (i.e. the same subspace) channel between Tx1 and Rx1 with specular point 803 shall be dropped, while channel between Tx2 and Rx1 with specular point 804 can be selected for further processing (unless it shall be dropped in view of other criteria in the channel-dropping criteria).

For each subspace and for each channel, PMB 109 calculates (604) a specular point (if any) on respective co-centric sphere and parameters of the respective specular point and compares the calculated parameters with the channel dropping criteria. For each given subspace, PMB 109 identifies (605) channels with parameters of respective specular points matching channel-dropping criteria, such channels referred to hereinafter as "omitted channels". For each given subspace, PMB 109 further generates (606) a set of selected channels. Generating the set of selected channels comprises excluding such identified omitted channels from further processing for image reconstruction and further matching the number of the remaining channels to the number $N_{ch}$ of channels predefined for the respective set. In order to match the number of channels in the set to the number $N_{ch}$, PMB 109 compares the amount of remaining channels (after exclusion of the omitted channels) with the number $N_{ch}$ predefined for the given subspace. When the amount of the remaining channels is less than the number $N_{ch}$, PMB 109 can generate "dummy" channels (channel with zero value of all time domain samples) to be added to the remaining channels to complete the set of the selected channels to the number $N_{ch}$. When the amount of the remaining channels is more than the number $N_{ch}$, PMB 109 matches the required number of selected channels by excluding the respective amount of remaining channel from further processing for image reconstruction. Such exclusion can be provided so as to maximize uniformity of coverage of a respective sphere (or predefined part thereof) by specular points of the selected channels.

Upon generating per-subspace sets of selected channels, PMB 109 provides (504) image reconstruction separately for each given subspace using collected data corresponding to the set of channels selected for the given subspace.

It is noted that a subspace size, a predefined number of selected channels and channel-dropping criteria can be configured differently for different inspection subspaces in the plurality of subspaces.

It is to be understood that the invention is not limited in its application to the details set forth in the description contained herein or illustrated in the drawings. The invention is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the presently disclosed subject matter.

It will also be understood that the system according to the invention may be, at least partly, a suitably programmed computer. Likewise the invention contemplates a computer program product embodied in a non-transitory computer readable medium for executing the method of the invention. The invention further contemplates a non-transitory machine-readable memory tangibly embodying a program of instructions executable by the machine for executing the method of the invention.

Those skilled in the art will readily appreciate that various modifications and changes can be applied to the embodiments of the invention as hereinbefore described without departing from its scope, defined in and by the appended claims.

The invention claimed is:

1. A method of security inspection by a security inspection system comprising ultra-wideband transmitters and receivers, the method comprising:
scanning a walk-through inspection space along with an inspected person passing there through to yield collected data informative of scattered signals in association with respective channels, wherein the ultra-wideband transmitters and receivers are arranged at both sides of the inspection space;
upon dividing the inspection space into a plurality of subspaces such that each voxel in the inspection space belongs to one and only one subspace, providing image reconstruction separately for each subspace of the plurality of the subspaces, wherein image reconstruction for voxels residing in a given subspace is provided using collected data corresponding to a set of channels selected for the given subspace, wherein selecting the set of channels comprises:
    identifying channels matching channel-dropping criteria defined to the given subspace thereby giving rise to omitted channels; and
    generating the set of channels selected for the given subspace, the generating comprising excluding the omitted channels from further processing for image reconstruction; and
using image reconstruction results to detect a concealed object.

2. The method of claim 1, wherein identifying channels matching channel-dropping criteria comprises calculating one or more parameters of specular points of channels reflected by a virtual equi-area tessellated sphere co-centric with a given subspace; and identifying channels with the calculated one or more parameters matching channel-dropping criteria defined to the given subspace thereby giving rise to omitted channels.

3. The method of claim 1, wherein the generating further comprises matching the amount of channels remaining after excluding the omitted channels to a predefined for the given subspace number $N_{ch}$ of selected channels and adding dummy channels when the amount of remaining channels is less than $N_{ch}$.

4. The method of claim 2, wherein the generating further comprises matching the amount of channels remaining after excluding the omitted channels to a predefined for the given subspace number $N_{ch}$ of selected channels and excluding a part of remaining channel from further processing for image reconstruction when the amount of remaining channels is more than $N_{ch}$, wherein the part of remaining channel is excluded so as to maximize uniformity of coverage of a predefined part of the virtual sphere by specular points of non-excluded channels.

5. The method of claim 2, wherein the channel-dropping criteria comprise one or more criteria selected from a group consisting of: absence of a specular point on a respective sphere, reflection angle more than a predefined maximal reflection angle, and max bore-sight angle for a receiver and/or for a transmitter more than a predefined maximal bore-sight angle.

6. The method of claim 2, wherein the channel-dropping criteria comprise one or more criteria related to location of respective specular points on the sphere.

7. The method of claim 1, wherein the channel-dropping criteria is configured the same for each subspace.

8. The method of claim 1, wherein inspection subspaces are combined in two or more groups corresponding to location in the inspection space, and channel-dropping criteria defined to subspaces in a given group comprise at least one criteria with values being common for all subspaces in the given group and being different for subspaces in another group.

9. The method of claim 8, wherein the at least one criteria with values being common for all subspaces in the given group, is related to location of specular points on respective spheres.

10. The method of claim 8, wherein the at least one criteria with values being common for all subspaces in the given group, is indicative of transmitter and receiver of a respective channel located at different sides of inspection space with regard to a walk direction.

11. A security inspection system comprising a signal acquisition unit operatively connected to data processing unit, wherein:
    the signal acquisition unit comprises a plurality of ultra-wideband transmitters and receivers arranged at both sides of a walk-through inspection space and configured to scan the inspection space along with an inspected person passing there through, to yield collected data informative of scattered signals in association with respective channels;
    the data processing unit is configured:
        upon dividing the inspection space into a plurality of subspaces such that each voxel in the inspection space belongs to one and only one subspace, to provide image reconstruction separately for each subspace of the plurality of the subspaces, wherein image reconstruction for voxels residing in a given subspace is to be provided using collected data corresponding to a set of channels selected for the given subspace, wherein selecting the set of channels comprises:
            identifying channels matching channel-dropping criteria defined to the given subspace thereby giving rise to omitted channels; and
            generating the set of channels selected for the given subspace, the generating comprising excluding the omitted channels from further processing for image reconstruction; and
        to use image reconstruction results for detecting a concealed object.

12. The security inspection system of claim 11, wherein identifying channels matching channel-dropping criteria comprises calculating one or more parameters of specular points of channels reflected by a virtual equi-area tessellated sphere co-centric with a given subspace; and identifying channels with the calculated one or more parameters matching channel-dropping criteria defined to the given subspace thereby giving rise to omitted channels.

13. The security inspection system of claim 11, wherein the generating further comprises matching the amount of channels remaining after excluding the omitted channels to a predefined for the given subspace number $N_{ch}$ of selected channels and adding dummy channels when the amount of remaining channels is less than $N_{ch}$.

14. The security inspection system of claim 12, wherein the generating further comprises matching the amount of channels remaining after excluding the omitted channels to a predefined for the given subspace number $N_{ch}$ of selected channels and excluding a part of remaining channel from further processing for image reconstruction when the amount of remaining channels is more than $N_{ch}$, wherein the part of remaining channel is excluded so as to maximize uniformity of coverage of a predefined part of the virtual sphere by specular points of non-excluded channels.

15. The security inspection system of claim 12, wherein the channel-dropping criteria comprise one or more criteria related to location of respective specular points on the sphere.

16. The security inspection system of claim 11, wherein the channel-dropping criteria is configured the same for each subspace.

17. The security inspection system of claim 11, wherein inspection subspaces are combined in two or more groups corresponding to location in the inspection space, and channel-dropping criteria defined to subspaces in a given group comprise at least one criteria with values being common for all subspaces in the given group and being different for subspaces in another group.

18. The security inspection system of claim 17, wherein the at least one criteria with values being common for all subspaces in the given group, is related to location of specular points on respective spheres.

19. The security inspection system of claim 17, wherein the at least one criteria with values being common for all subspaces in the given group, is indicative of transmitter and receiver of a respective channel located at different sides of inspection space with regard to a walk direction.

20. A non-transitory computer readable medium usable in conjunction with security inspection system comprising ultra-wideband transmitters and receivers arranged at both sides of a walk-through inspection space, the media comprising instructions that, when executed by a computer, cause the computer to perform operations comprising:
upon dividing the inspection space into a plurality of subspaces such that each voxel in the inspection space belongs to one and only one subspace, providing image reconstruction separately for each subspace of the plurality of the subspaces,
wherein image reconstruction for voxels residing in a given subspace is provided using collected data corresponding to a set of channels selected for the given subspace,
wherein the collected data are obtained by scanning the inspection space along with an inspected person passing there through and are informative of scattered signals in association with respective channels, and
wherein selecting the set of channels comprises:
identifying channels matching channel-dropping criteria defined to the given subspace thereby giving rise to omitted channels; and
generating the set of channels selected for the given subspace, the generating comprising excluding the omitted channels from further processing for image reconstruction; and
using image reconstruction results to detect a concealed object.

* * * * *